United States Patent [19]

Halm

[11] 4,360,584

[45] Nov. 23, 1982

[54] METHOD OF PHOTOPOLYMERIZATION WITH COMPLEX METAL CHELATE CATALYSTS

[75] Inventor: James M. Halm, Lombard, Ill.

[73] Assignee: A. B. Dick Company, Niles, Ill.

[21] Appl. No.: 245,158

[22] Filed: Mar. 18, 1981

[51] Int. Cl.³ .......................... G03C 1/68; G03C 1/66
[52] U.S. Cl. .................................... 430/286; 430/287; 430/927; 430/307; 204/159.23; 204/159.24
[58] Field of Search ................. 430/286, 287, 927, 83; 204/159.23, 159.24

[56] References Cited

U.S. PATENT DOCUMENTS

| 3,016,297 | 1/1962 | Mochel et al. | 430/927 |
| 4,123,268 | 10/1978 | Halm | 430/83 |
| 4,153,769 | 5/1979 | Halm | 526/195 |
| 4,160,667 | 7/1979 | Halm | 96/15 R |

FOREIGN PATENT DOCUMENTS

| 2749768 | 5/1979 | Fed. Rep. of Germany . | |
| 1188330 | 9/1967 | United Kingdom | 430/96 |

Primary Examiner—John E. Kittle
Assistant Examiner—John L. Goodrow
Attorney, Agent, or Firm—McDougall, Hersh & Scott

[57] ABSTRACT

Method of photopolymerization to produce vinyl based polymers and copolymers in the presence of a catalyst in the form of complex metal chelates.

13 Claims, No Drawings

METHOD OF PHOTOPOLYMERIZATION WITH COMPLEX METAL CHELATE CATALYSTS

This invention relates to a method for polymerization of unsaturated monomers in the presence of Group IIIA chelates as a photocatalyst.

Photocatalytic polymerization of polymerizable monomers is advantageous from the standpoint that polymerization can be carried out under especially mild conditions whereby a polymer of higher molecular weight can be produced with greater purity of comparison with the more destructive thermal polymerization processes. A photopolymerization process also utilizes less energy and provides the pathway to the production of polymers incapable of otherwise being produced. In addition, the photopolymerization process of this invention provides effects associated with imaging in terms of light and shadow unique to the photochemistry involved.

In my previously issued U.S. Pat. No. 4,153,769, issued May 8, 1979, and entitled "Vinyl Polymerization with Boron Chelates as Catalyst and Photoconductive Sensitizer," description is made of a series of boron chelates as initiators to catalyze the thermal polymerization of vinyl monomers and comonomers, particularly N-vinyl carbazoles and derivatives thereof, and wherein when the catalyst component is allowed to remain, the polymer or copolymer exhibits organic photoconductive properties to enable use as a photoconducting material.

In my copending application Ser. No. 153,881, filed May 27, 1980; which is a continuation-in-part of application Ser. No. 131,150, filed Mar. 17, 1980; which is a continuation of application Ser. No. 897,719, filed Apr. 19, 1978 (now abandoned); filed as a continuation-in-part of application Ser. No. 738,147, filed Oct. 29, 1976, and entitled "Photoconductive Coating and Compositions" (now abandoned), description is made of a series of acceptor-sensitizer compounds in the form of metal chelates which exhibit photosensitive and photoconductive properties that enable their use in the production of photoconductive elements.

It has been found, in accordance with the practice of this invention, that the boron chelates of the aforementioned issued patent and the acceptor-sensitizer compounds of the aforementioned copending application find benefit used as Group IIIA catalyst in the polymerization to form vinyl polymers and copolymers by photopolymerization technique. Photopolymerization with the Group IIIA chelate catalysts of the type described can be carried out in solution or in amorphous films. The described Group IIIA chelate catalysts are effective to cause photopolymerization of such unsaturated monomers in the presence of actinic radiation within the blacklight range and within the visible region of 300–800 μm. Light of a wavelength suitably matched to the charge-transfer spectrum of the metal chelate complex is particularly effective. The mechanism of the polymerization is believed to involve the charge-transfer complex formed from a monomeric donor and acceptor compounds to form the polymer.

The photocatalyst employed in the practice of this invention may be represented by the following general formula

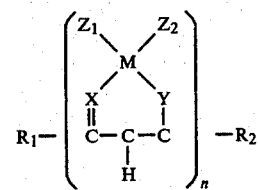

in which M is a metal or metalloid entity such as aluminum, gallium, indium, thalium, but preferably boron; X and Y, which may be the same or different, are selected of the group consisting of sulphur, nitrogen, phosphorus, antimony, selenium, and preferably oxygen; $Z_1$ and $Z_2$, which may be the same or different, preferably are fluorine, but instead may be another halogen such as chlorine or bromine; an aryl, alkaryl or heterocyclic group, such as phenyl, tolyl, naphthyl, anthracyl, furyl, pyrryl, idolyl, pyrimidyl, pyridyl and furfuryl, or substituted derivatives thereof in which the substituents can be halogen, such as chlorine, bromine, fluorine, iodine; alkoxy groups such as methoxy, alkoxy or other $C_1$–$C_{10}$ alkoxy groups, or other aryl, alkaryl or heterocyclic group of the type described above such as phenoxy; alkylates such as acetate, propionate, or other $C_2$–$C_{10}$ alkylate, or an oxygen substituted ligand; $R_1$ and $R_2$ may be the same or different and may be aryl or alkaryl, such as phenyl, totyl, naphthyl, anthracyl and the like, and substituted derivatives thereof in which the substituents are as defined above, and preferably halogen or electron-withdrawing groups such as $CF_3$; alkyl or alicyclic groups or substituted derivatives thereof in which the substituents are as defined above and in which the alkyl group is methyl, ethyl, propyl, isopropyl, butyl, isobutyl, tertiary butyl, or other $C_1$–$C_{10}$ alkyl, and in which the alicyclic groups are cyclopropyl, cyclobutyl, cyclopentyl and the like; n is 1–3 and when n is 1 $R_1$ can be

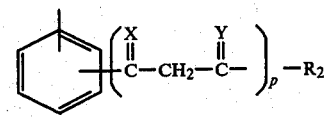

in which p is either 1 or 2.

In addition, it has been found that compounds of the general formula below also function as photocatalysts. The symbols have the same meaning as previously defined.

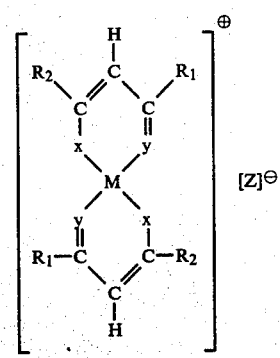

The reaction of the ligand of a β-diketone or similar derivative will sometimes give an ionic chelate compound. The reactions of boron trichloride (in contrast to boron trifluoride) to give mononuclear ring chelates of ionic character was described by Morgan & Turnstall (and references cited therein) J. Chem. Soc., 125:1963 (1924).

A multinuclear indium chelate compound has now been shown, by chlorine analysis, to have this type of structure in the present application. Halogen analysis of the gallium chloride chelate, however, indicates the non-ionic alternative.

The following are illustrative of the Group IIIA photocatalysts which may be employed in the photo polymerization process of this invention:

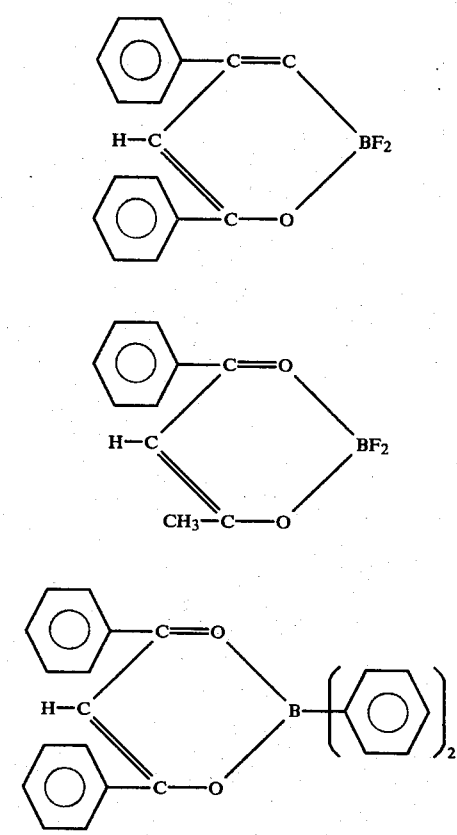

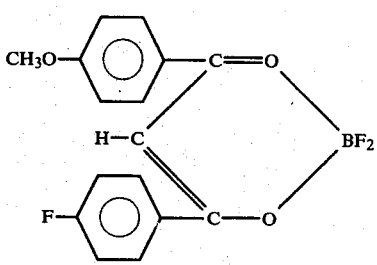

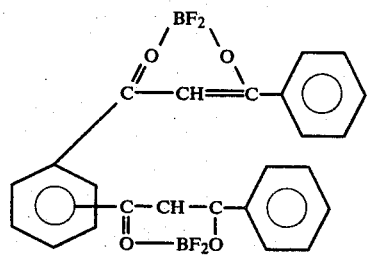

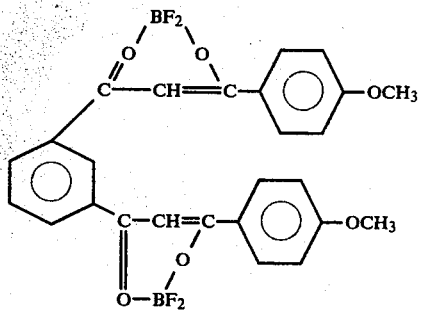

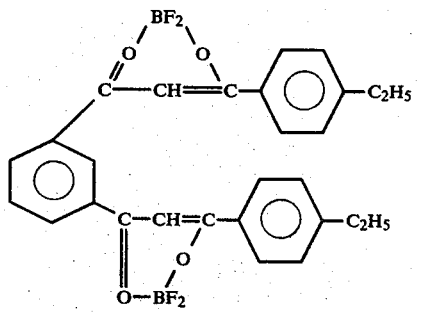

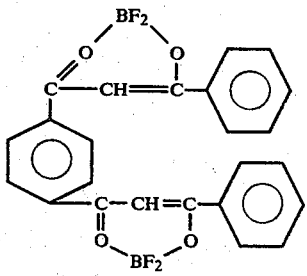

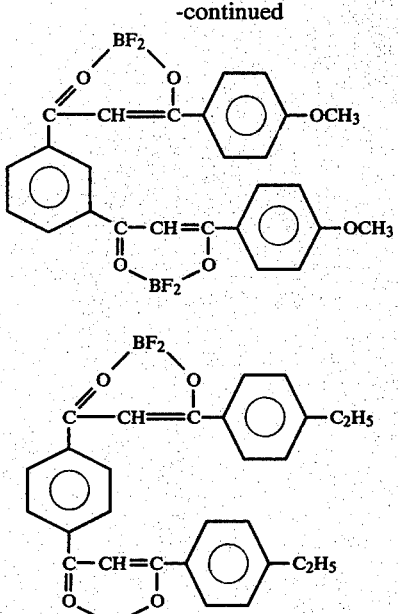 (10)
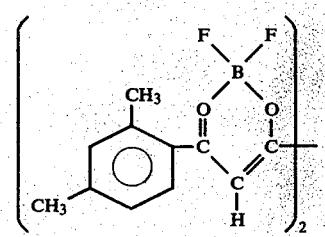 (11)
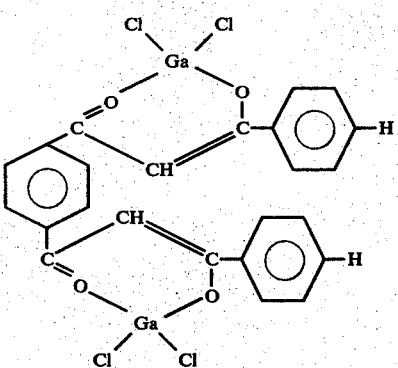 (12)
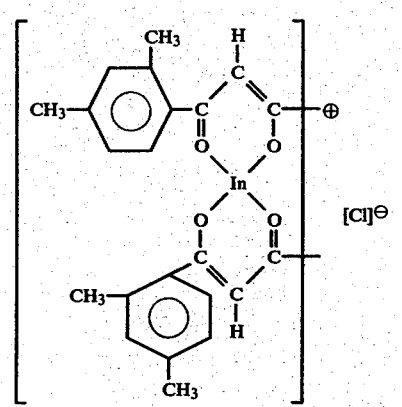 (13)
(14)
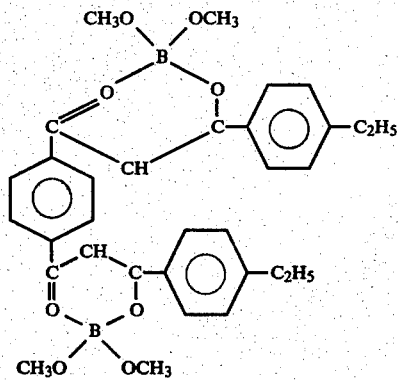 (15)
Chelate Compound.
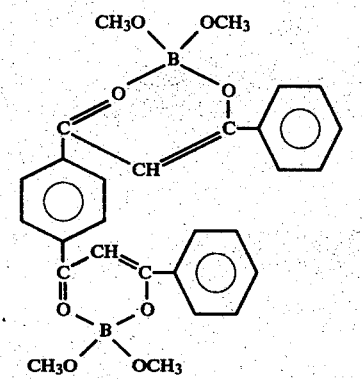 (16)
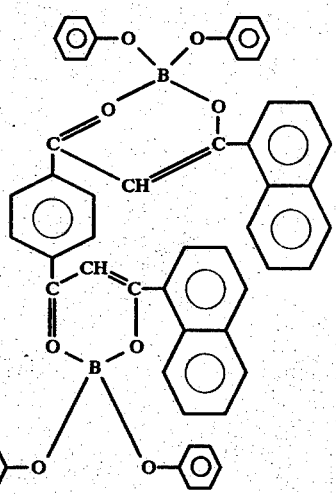 (17)

-continued

(18)
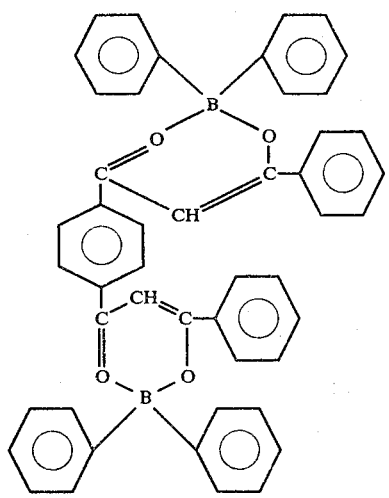

(19)
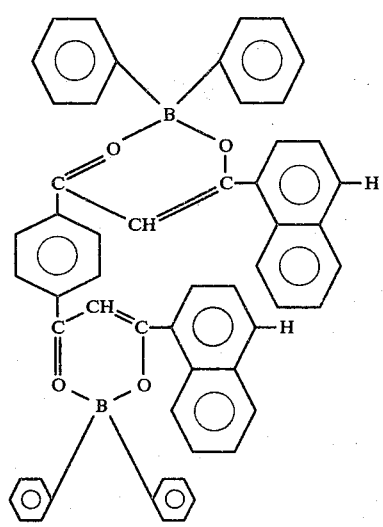

(20)
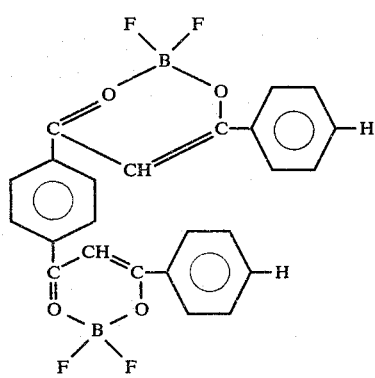

-continued (21)

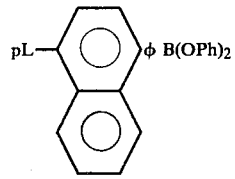

= pLH φ B(OPh)$_2$ (22)

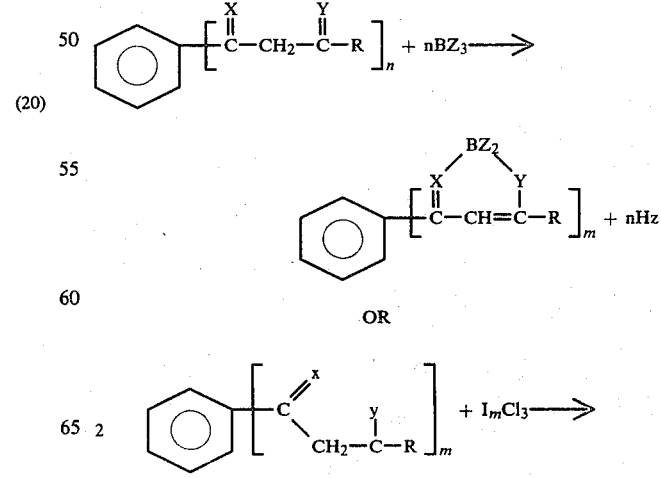

The fundamental reaction in the preparation of the photocatalytic chelate complexes employed in the practice of this invention, involves the chelation of an appropriate ligand, as illustrated by the following equation in which a BZ$_2$ moiety is used as the chelating component:

$$\text{Ph}\left[\underset{\|}{\overset{X}{C}}-CH_2-\underset{\|}{\overset{Y}{C}}-R\right]_n + nBZ_3 \longrightarrow$$

$$\text{Ph}\left[\overset{BZ_2}{\underset{C-CH=C-R}{X\diagup\diagdown Y}}\right]_m + nHz$$

OR $$2\,\text{Ph}\left[\underset{\|}{\overset{x}{C}}-CH_2-\underset{\|}{\overset{y}{C}}-R\right]_m + I_mCl_3 \longrightarrow$$

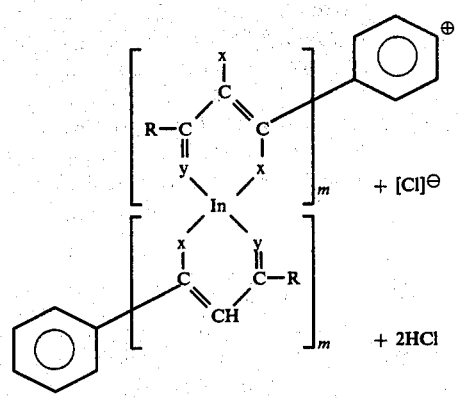

The preparation of ligand and chelate as given does not lead to the compounds subsequently labeled as this document indicates.

A number of routes can be used to obtain the appropriate ligand, one of which is illustrated by the following equation:

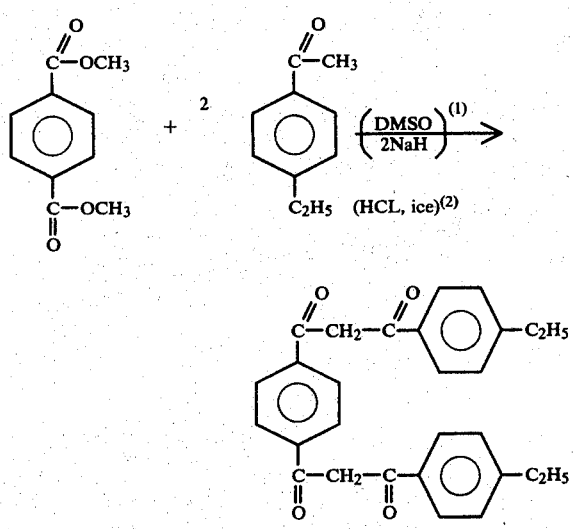

In a preferred mode of preparation, a phthallato ester is reacted with an alkyl ketone in a Cross Claisen condensation reaction, followed by chelation with a $BF_3$ etherate.

The following are representative of the preparation of photocatalytic chelate compounds employed in the practice of this invention.

EXAMPLE 1

Preparation of ligand (for compound 11)

15 grams sodium hydride in oil suspension are stirred into 150 ml of dimethyl sulfoxide at room temperature during a 15 minute period. 39 grams of dimethyl terephthalate with stirring. A nitrogen bubbler is attached with a condenser in a three-necked flask and the reaction is carried out under a nitrogen blanket. 59 grams of 4'-ethylacetophenone in 100 ml of dimethyl sulfoxide are added dropwise from a dropping funnel. The exothermic reaction is moderated, as foaming occurs, by an ice water bath. The reaction mixture is allowed to stand for two hours after the ethylacetophenone has been added and is then heated cautiously to 50° C. and held at that temperature for three hours. The reaction mixture is allowed to cool to ambient temperature and then is maintained at that temperature overnight.

The red reaction mixture is poured onto ½ liter of ice and the resulting yellow solid is dissolved in 200 ml of methylene chloride which is washed two times with 100 ml of water and two times with 100 ml of a saturated sodium bicarbonate solution.

The methylene chloride solution is dried over sodium sulphate and concentrated to one-third the original volume on a steam line. The methylene chloride solution is placed in a freezer at 0° C. and the precipitate is collected by vacuum filtration to yield a ligand having the following chemical structure:

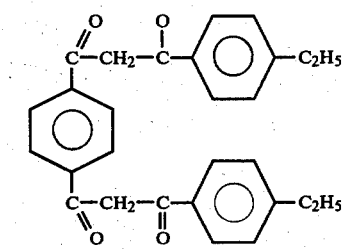

Preparation of chelate (11)

0.048 mole of the ligand is added to 200 ml of 1,2-dimethoxyethane solvent. The mixture is heated to 50° C. with stirring under a nitrogen blanket. 0.096 mole of trifluoroboron etherate, dissolved in 50 ml of 1,2-dimethoxyethane solvent is added dropwise. The mixture is brought to reflux temperature (about 83° C.) and held at reflux for four hours. The solvent is stripped to one-third its original volume and the concentrate is cooled to ambient temperature and poured into high boiling petroleum ether. The mixture is cooled overnight at 0° C. and the resulting precipitate (compound 11) is removed by filtration under vacuum.

The precipitate is purified by fractionation in a Soxhlet extractor using acetone as solvent. % C found=64.51; % H found=4.85; % C calc.=64.39; % H calc.=4.64: M.P.=dec. 220° C.

EXAMPLE 2

In the preparation of the dichelate, represented by the formula (10), the 4-ethylacetophenone in Example 1 was replaced by equal moles of 4'-methoxyacetophenone and the terephthalate was replaced by the metaphthalate.

EXAMPLE 3

In the preparation of the compound represented by the formula (9), Example 1 was followed except that the 4'-ethylacetophenone was substituted by an equivalent amount of acetophenone.

EXAMPLE 4

The compounds 1, 2, 3, 4 and 5 were prepared according to teachings of the primary literature; see H. S. Booth & D. R. Martin, Boron Trifluoride and its Derivitives, John Wiley, New York, 1949; and references therein.

EXAMPLE 5

An oxalato-chelate (12) was prepared as in Example 1 except that 2',4'-dimethylacetophenone was substituted for equivalent amounts of the 4'-ethylacetophenone and ethyl oxylate was substituted for the terephthalate. % C found = 59.35; % H found = 4.68; % C calc. = 59.22; % H calc. = 4.52.

EXAMPLE 6

The preparation of a photocatalyst compound in which M is gallium and is represented by the structural formula (13) The ligand

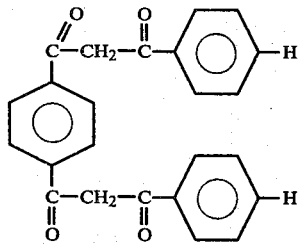

was prepared as described in the preparation of the boron dionates.

The solvent, dimethoxyethane, was dried and degassed as indicated before. Three grams of ligand was dissolved in the solvent which was heated to near reflux. As before, the reaction contents were protected from the atmosphere with a nitrogen bubbler. About two equivalents (~3 grams) of anhydrous Ga $Cl_3$ was dissolved in ~100 ml of dimethoxyethane and added dropwise to the refluxing ligand solution over an hour time. Reflux was continued during the working day for three days. The heat was disconnected to the reaction over night.

The dimethoxyethane solution was distilled to half volume, cooled, and added to twice the volume of heptane. A viscous oil separated. The heptane was evaporated to ~1/5 volume to yield some unreacted ligand.

The oil was diluted with methanol and this methanol solution was filtered. It was dried over sodium sulfate, filtered, and taken to dryness. This hygroscopic solid was dried in a dessicator. Chlorine analysis suggests the composition given in structure (13) % Cl found = 22.5;/% Cl calc. = 21.8.

EXAMPLE 7

The preparation of a photocatalyst compound in which M is indium as represented by the structural formula (14). The ligand

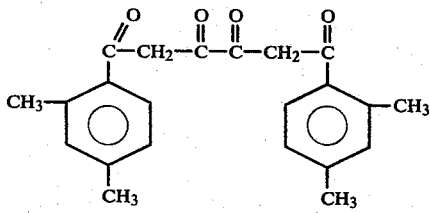

is the same as that prepared in example 5.

The solvent was prepared as indicated before and the general features of the preparation were similar to those involved for the preparation of the gallium compound. After reflux for three working days, the reaction was cooled and produced ¾ of the original weight of ligand. The deep red-brown solution remaining after ligand isolation, was taken to dryness and diluted with methanol. A red-brown solution resulted together with a red-brown solid. This mixture was set in the freezer for a day after which the solid was filtered off. Total yield was ~0.4 gram. Chlorine analysis suggests a structure more consistent with an ionic compound than a neutral chelate. % Cl found = 6%; % Cl calc. = 7%. The structure (14) would be consistent with the analysis.

In the following examples, a diketone is chelated with an alkoxy boron ester as illustrated by the following reaction:

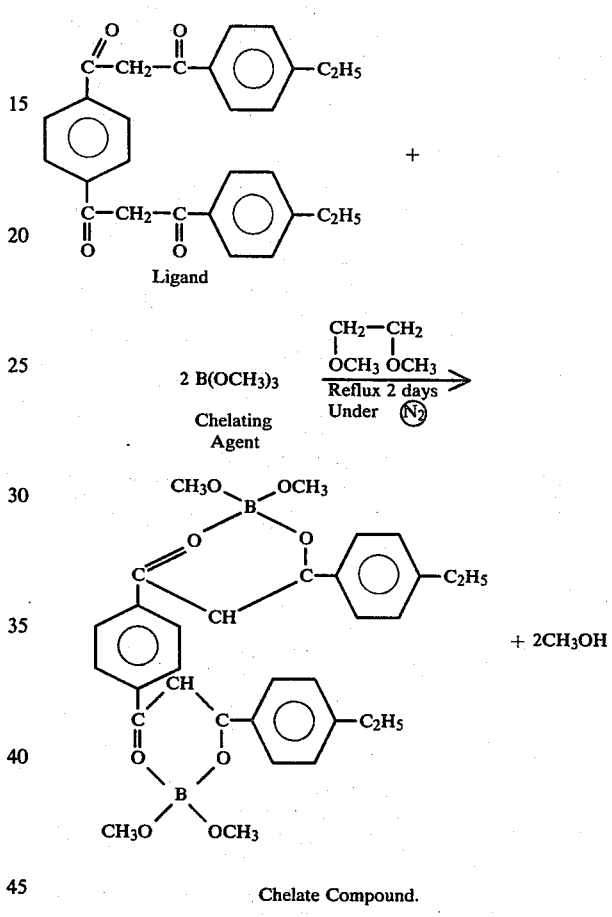

Chelate Compound.

EXAMPLE 8

Equivalent portions of reactants were kept at reflux of dimethoxyethane for two days under an envelope of $N_2$. A five gram portion of bis (ketone) above and 2.45 g of $B(OCH_3)_3$ were dissolved in 200 ml of degassed dimethoxyethane and brought to reflux. At the end of two days, ½ volume of the dimethoxyethane was distilled off under a $N_2$ stream and the reaction contents brought to room temperature. An equal volume of petroleum ether was added to increase the precipitation of solid and the mixture set in the freezer overnight. The deep yellow reaction product was vacuum filtered and washed with cold petroleum ether. The amount of solid isolated was 1.4 grams which amounted to 52% yield. It was recrystallized from THF to give a bright yellow solid with a M.P. >320° C. with decomposition.

EXAMPLE 9

The ligand of example 9 is replaced in equivalent molar amounts with others of the ligand of the previous examples to produce the corresponding dimethoxy chelate.

EXAMPLE 10

The process of examples 9 and 10 is followed except that the B(OCH$_3$)$_3$ is replaced by corresponding molecular amounts of chelating agents in which the boron is replaced by another metal such as aluminum gallium, indium, or thallium and the alkoxy group on the boron, aluminum, gallium, indium or thallium is replaced with an alkyl group such as ethyl, methylpropyl, butyl, pentyl, cyclopentyl and the like, an alkanyl group such as phenyl, tolyl, anthracyl and the like or a heterocyclic group such as furfuryl, pyrryl, idoyl, pyrimidyl, pyridyl and furfuryl including substituted and unsubstituted derivatives of the above or other alkoxy groups or in which R is an alkyl aralkyl or heterocyclic group substituted or unsubstituted as defined above.

Photopolymerization can be carried out with the Group IIIA complex chelates described to form polymers and copolymers of monomers capable of addition polymerization through unsaturated carbon to carbon linkages. Representative are the vinyl monomers, such as vinyl chloride, vinyl acetate, and particularly the vinyl carbazoles to form homopolymers and copolymers thereof with other copolymerizable unsaturated monomers such as the acrylates, alkylacrylates, styrene, styrene derivatives and the like.

Representative of the vinyl carbazoles which can be polymerized by photo techniques in accordance with the practice of this invention are illustrated by the following structural formulae:

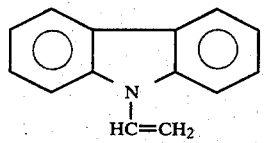
(23)

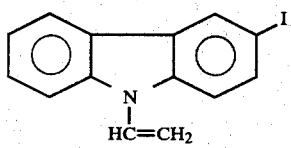
(24)

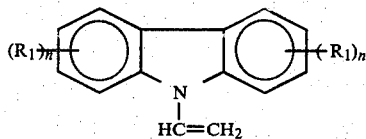
(25)

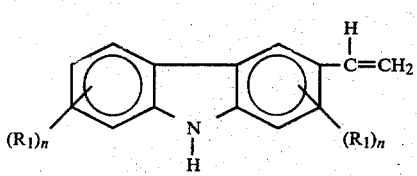
(26)

The following examples will illustrate the photo polymerization reaction in accordance with the features of this invention:

EXAMPLE 11

A formulation was made using 10% (1) and 90% N-vinylcarbazole solution in 60%/40%=THF/Cyclohexanone adjusted to 20% in solids. A thin layer of this solution was applied to a glass plate kept under daylight fluorescent radiation from ambient room lighting. The measured intensity of radiant flux at the surface of the plate as measured by a Model IIIA United Detector Technology radiometer was 120 ($\mu$watt)/cm$^2$. After 20 hours, the recovered solid had changed in color from yellow to deep orangish brown. When redissolved in tetrahydrofuran (THF), this material was now capable of forming a film attributed to the polymer polyvinyl carbazole (PVK).

Repeating the experiment in the absence of (1) caused no noticeable change and this N-vinylcarbazole solution was incapable of producing a film after solvent evaporation.

EXAMPLE 12

A formulation was made using 3 grams of ethylcellulose, 2 g. of N-vinylcarbazole, and 0.1 gram of (4) in 30 ml of methylethylketone. A #40 wire wound rod was used to make a coating of this formulation onto a paper with low absorbance or hold-out like X904 Allied basestock, and the coating was air-dried at room temperature overnight. This coating was covered with a positive film mask and the assembly placed under a small U.V. light source (Westinghouse 8 w Blacklight Bulb)—at a distance of 5 inches for 15 minutes. The coated paper was placed face down against an uncoated paper substrate and this assembly was passed through rollers heated between 200° and 300° F. An imagewise transfer of film occurred in the non-light struck areas while the light struck areas were retained on the coated substrate. A critical adjustment of temperature made possible this transfer for 15 cycles. The original substrate after these fifteen transfers had relief depressions on it in mirror image to the transfer. A similar trial without compound (4) caused indiscriminate transfer without any information conveyance. The imagewise transfer of information is taken to be evidence for polymerization of the film in light-struck areas where the melting point is much higher than areas where monomers as N-vinylcarbazole or other materials are not polymerized.

EXAMPLE 13

A formulation was prepared using an 80/20(%)=toluene/C$_2$H$_5$OH solvent of concentration 3 g/60 ml in ethylcellulose (Hercules K=50), 4 g/60 in Epocryl Resin 370 (Shell Chemical), and 0.1 g/60 ml in (4). This formulation was coated onto a substrate of X904 applied basestock paper with a #40 wire wound rod. This coating was left to dry at ambient conditions overnight. The coating was imaged through a positive using a "Nu-Arc" high intensity photo arc-carbon source at a distance of one meter from the source for ½ minute.

The transfer of the coating in non light-struck areas, to a receiving sheet of similar kind upon passage through twin rollers at 200°-300° F., is indicative of polymerization of the acrylate monomer (Epocryl) in light struck areas.

At 250°-270° F. multiple transfers were made to approximately 15 receiving sheets. The original coating, after the transfer process, had a relief image on it corresponding to transferred areas.

A blank with ethylcellulose and N-vinylcarbazole monomer was prepared as before and exposed for 1.5 minutes through a high contrast positive mask on the carbon arc apparatus. When this coated blank (no sensitizer) was processed through heated rollers at 290° F., some coating was transferred but no image information as indicated on the positive target. The coating was run through the rollers in contact with the receiving sheet for two additional trials without information being transferred from the positive target. This blank result is in contrast to the information transfer effect which occurred when the chelate sensitizer was used.

EXAMPLE 14

A THF solution was prepared in which the concentration of ethylcellulose was 3.8 g/75 ml, N-vinylcarbazole 2 g/75 ml and compound (4) was 0.2 g/75 ml. This solution was coated onto a substrate (Allied X904 basestock). A #40 wire wound rod was used to meter the coating which was left to dry overnight. The coating was imaged through a high contrast positive for 15 minutes at 3 inches from a two (daylight fluorescent) bulb source (15 watts each bulb). The measured radiant intensity at the surface of the coating was $2.7 \times 10^3$ $\mu$watt/cm$^2$. The imaged area (non-polymerized) was transferred by heated rollers to a receiving copy at temperatures between 200° and 300° F.

A control formulation was prepared without compound (4) as above. One coating was exposed for 15 minutes through the same mask with the same light source. The coating was matched up with a receiving sheet and passed through heated rollers (1st time at 245° F.; 2nd time at 295° F.). In each case, a transfer of the coating was made without any image formation. The fluorescence of the carbazole, when viewed in the dark, is a sensitive gauge to determine any transfer of an image. A similar coating was exposed through the same light source for 45 minutes. The coating was matched up with a receiving sheet and passed three times through heated rollers at 295° F. In each case, some coating from the original sheet was transferred to the receiving sheet. No image was transferred, however, and no image was formed, by the process, on the originally exposed sheet.

EXAMPLE 15

A toluene/C$_2$H$_5$OH=80/20(%) solution was prepared in which the concentration of ethylcellulose was 3 g/60 ml, of 2-ethylvinylhexanoate was 8 g/60 ml, and of (1) was 0.2 g/60 ml. This solution was coated onto a substrate like Allied X904 basestock paper. A #40 wire wound rod was used to meter the coating which was left to dry overnight. The coating was imaged through a high-contrast positive with the source in Example 15. The non-polymerized portion was heat transferred to a receptor sheet while the polymerized material was not transferred. Transfer occurred between heated rollers at between 250°–300° F. in imagewise fashion. The imagewise transfer is taken as evidence for the polymerization by light in the light struck areas of the target. The areas which were blocked to light were capable of being heat transferred as low melting monomeric mixtures.

EXAMPLE 16

A 0.5 g portion of (1) was dissolved in 30 ml of dimethoxyethane. To this solution was added 5 g of N-vinylcarbazole. Upon addition of the carbazole, the almost colorless solution turned to a deep yellow-brown. The solution was irradiated in a 60 ml test tube (pyrex) at 354 $\mu$m for 1.5 hours by the U.V. light source described in Example 13. This source was mounted so that the test tube, container, and fluorescent bulb were parallel and at a distance of 2 inches. The solution was placed in a dark cabinet overnight. The next morning the solution was coated onto an aluminum substrate with a #60 wire wound rod. The solution formed a tough adhesive brown-orange film on the aluminum substrate. This film was dried overnight and placed in the oven at 100° C. for 10 minutes. The following day it was dark adapted for 24 hours, and the following data show it to have photoconductive properties:

|  | decay curve sensitivity to t(1/e) | charge (volts) acceptance | dark decay (volts/sec) |
| --- | --- | --- | --- |
| $\oplus$ mode | 173 $\mu$J/cm$^2$ | 500 | 8 |
| $\ominus$ mode | 1080 $\mu$J/cm$^2$ | 170 | 27 |

This illustrates a case where the photopolymerization catalyst (1) simultaneously sensitizes the polymer so that the mixture can be coated to form a photoconductive film.

EXAMPLE 17

A 0.15 g portion of (21) was dissolved in 10 ml of dimethoxyethane. In this solution was dissolved 1.5 g of (24). Upon the addition of the iodo compound, the solution turned a deep yellow-brown. The solution was irradiated in a 40 ml test tube at 354 $\mu$m for 4 hours by the U.V. light source described in Example 13. The source was mounted so that the test tube container and fluorescent bulb were parallel and at a distance of 2 inches. The solution was placed in a dark cabinet overnight and the next morning, the solution was coated onto an aluminum substrate with a #60 wire wound rod. The resulting film provided electrophotographic properties.

|  | decay curve to t(1/e) | charge acceptance | dark decay |
| --- | --- | --- | --- |
| $\oplus$ mode | 102 $\mu$J/cm$^2$ | 320 volts | 8 volt/sec |

This illustrates a case where the photopolymerization catalyst (21) simultaneously sensitizes the polymer so that the mixture can be coated to form a photoconductive film.

EXAMPLE 18

A solution and coating were prepared as in Example 17 but with 0.6 g of (22) as the acceptor and (23) as the donor. The coating was curred for 10 minutes after being air dried for 24 hours. The electrophotographic properties were:

|  | decay curve to t(1/e) | charge acceptance | dark decay |
| --- | --- | --- | --- |
| $\oplus$ mode | 3,240 $\mu$J/cm$^2$ | 340 volts | 6 volts/sec |

This example illustrates a case where the photopolymerization catalyst (22) simultaneously sensitizes the polymer so that the mixture can be coated to form a photoconductive film.

EXAMPLE 19

In order to test the efficacy of the chelate sensitizers, a comparison was made of the effect of the V.V. light on the monomer solutions without the chelate sensitizers being present.

A 10% (23) solution in 80/20=THF/cyclohexanone was irradiated for two hours in the same make test tube as in Example 17, at a distance of ½ inch for two hours.

The contents were poured into methanol. No precipitation occurred. This effect is in contrast to the reaction product obtained in Example 16 which produced a copious precipitate (polymer) when poured into methanol.

The other half of the contents were used to make a coating on an aluminum substrate. When the evaporation of solvent occurred a crystalline white deposit was left in contrast to the tough film obtained when the chelate sensitizer was used in Example 16.

One gram of (24) was dissolved in 5 ml of 80/20(%)=THF/cyclohexanone. The solution was irradiated at 354 μm as described in Example 18 for 5 hours at ½ inch. The tube was set in the dark overnight. The next day, ½ the solution was poured into methanol producing a white precipitate. The other ½ was coated onto an aluminum substrate to give a film contaminated by a white powder. The irradiation experiment was repeated with 2.5 g of (24). The precipitated polymer was isolated by filtration and washed twice with methanol. The solid was dried by drawing air through it for two hours. The total weight of the polymer was 1.2 g or 50% conversion. The methanol precipitation material was taken to dryness and the remaining monomer was recovered and redissolved in the same solvent as before and again irradiated. No additional polymer was recovered.

While in this case the compound (24) was shown to produce some polymer without the initiator and sensitizer being present, the film produced was highly contaminated with monomer compared to the transparent film obtained from use of the sensitized reaction.

In this case the iodo group itself sensitizes the monomer to some polymerization without a catalyst being present. However, the chelates produce a tough hard film without the residual monomer making a major impact.

I claim:

1. In the photopolymerization of unsaturated monomers to form the corresponding polymers and copolymers the improvement wherein the polymerization is carried out upon exposure to light in the presence of Group IIIA catalyst in the form of a complex metal chelate having the structural formula

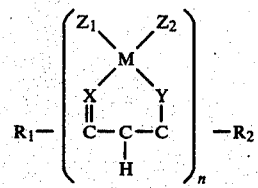

in which M is a metal or metalloid selected from the group consisting of aluminum, gallium, indium, thalium and boron, X and Y are groups selected from the group consisting of sulphur, nitrogen, phosphorus, antimony, selenium and oxygen, $Z_1$ and $Z_2$ are groups selected from the group consisting of a halogen and substituted and unsubstituted alkyl, aryl, alkaryl, alkoxy, aryloxy, alkaryloxy and heterocyclic groups selected from the groups consisting of furyl, pyrryl, iodyl, pyrimidyl, pyridyl and furfuryl, $R_1$ and $R_2$ are groups selected from the group consisting of substituted and unsubstituted aryl, alkaryl, alkyl and alicyclic groups, n is a number of 1 to 3, and when n is 1, $R_1$ may be a group having the general formula

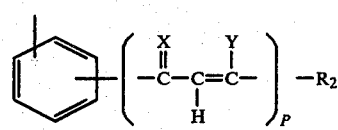

in which p is a number of 1 or 2 and $R_2$, X and Y have the same meaning as defined above.

2. In the photopolymerization of unsaturated monomers to form corresponding polymers and copolymers the improvement wherein polymerization is carried out upon exposure to light in the presence of a group III catalyst in the form of a complex metal chelate having the structural formula

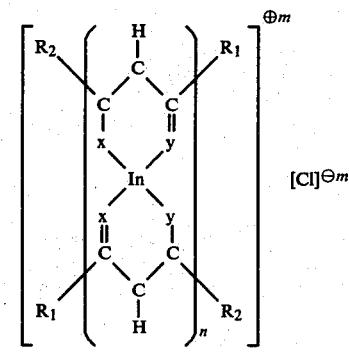

in which x and y are groups selected from the group consisting of sulphur, nitrogen, phosphorous, antimony, selenium and oxygen, $R_1$ and $R_2$ are groups selected from the group consisting of substituted and unsubstituted aryl, alkaryl, alkyl and alicyclic groups, m is a number of from 1 to 3 and when n is 1, $R_1$ may be a group having the general formula

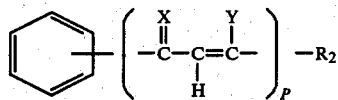

in which P is a number of 1 or 2, $R_2$, x and y have the same meaning as defined above.

3. The method as claimed in claims 1 or 2 in which the polymer that is formed is a vinyl based polymer or copolymer.

4. The method as claimed in claims 1 or 2 in which the monomer is a vinyl carbazole or derivative thereof.

5. The method as claimed in claims 1 or 2 in which the photopolymerization is carried out while the monomer or monomers are in solvent solution.

6. The method as claimed in claim 1 in which the photopolymerization is carried out upon exposure to actinic radiations within the blacklight range or a range within 300–800 μm.

7. The method as claimed in claims 1 or 2 in which the photopolymerization is carried out while the monomer or monomers are distributed in a film.

8. The method as claimed in claims 1 or 2 in which the monomer is a vinyl ester.

9. The method as claimed in claims 1 or 2 in which the monomer is an acrylate.

10. The method as claimed in claims 1 or 2 in which the polymerization simultaneously sensitizes the film of polymer as a photoconductor.

11. The method as claimed in claims 1 or 2 which enables the exposed film to be imagewise transferred to a receptive substrate upon the application of heat.

12. The method as claimed in claim 11 which enables image-wise transfer of multiple images to a receptive substrate.

13. The method as claimed in claims 1 or 2 which enables a relief image (Intaglio) to be formed from transfer of non-polymerized monomer.

* * * * *